United States Patent
Nakashima et al.

(10) Patent No.: US 10,456,433 B2
(45) Date of Patent: Oct. 29, 2019

(54) SUPPRESSIVE AGENT FOR RHEUMATOID ARTHRITIS, PROPHYLACTIC AGENT FOR RHEUMATOID ARTHRITIS, THERAPEUTIC AGENT FOR RHEUMATOID ARTHRITIS, AND FOOD FOR SUPPRESSING RHEUMATOID ARTHRITIS

(71) Applicant: euglena Co., Ltd., Tokyo (JP)

(72) Inventors: Ayaka Nakashima, Yokohama (JP); Yuta Asayama, Yokohama (JP); Osamu Iwata, Yokohama (JP); Kengo Suzuki, Yokohama (JP)

(73) Assignee: euglena Co., Ltd., Tokyo (JP)

( * ) Notice: Subject to any disclaimer, the term of this patent is extended or adjusted under 35 U.S.C. 154(b) by 151 days.

(21) Appl. No.: 15/563,993

(22) PCT Filed: Apr. 7, 2016

(86) PCT No.: PCT/JP2016/061386
§ 371 (c)(1),
(2) Date: Oct. 3, 2017

(87) PCT Pub. No.: WO2016/163454
PCT Pub. Date: Oct. 13, 2016

(65) Prior Publication Data
US 2018/0133271 A1    May 17, 2018

(30) Foreign Application Priority Data
Apr. 8, 2015 (JP) .................................. 2015-079525

(51) Int. Cl.
| | |
|---|---|
| *A61K 36/05* | (2006.01) |
| *A61K 35/68* | (2006.01) |
| *A23L 33/10* | (2016.01) |
| *A61P 19/02* | (2006.01) |
| *A61K 45/06* | (2006.01) |

(52) U.S. Cl.
CPC .............. *A61K 36/05* (2013.01); *A23L 33/10* (2016.08); *A61K 35/68* (2013.01); *A61K 45/06* (2013.01); *A61P 19/02* (2018.01); *A23V 2002/00* (2013.01)

(58) Field of Classification Search
CPC ..................................................... A61K 36/05
USPC ......................................................... 424/725
See application file for complete search history.

(56) References Cited

U.S. PATENT DOCUMENTS

| | | |
|---|---|---|
| 2006/0246556 A1 | 11/2006 | Napier et al. |
| 2010/0154080 A1 | 6/2010 | Das et al. |
| 2011/0016585 A1 | 1/2011 | Pereira et al. |
| 2012/0329752 A1 | 12/2012 | Suzuki |

FOREIGN PATENT DOCUMENTS

| | | |
|---|---|---|
| JP | 08-301875 A | 11/1996 |
| JP | 2006-511233 A | 4/2006 |
| JP | 3839836 B1 | 11/2006 |
| JP | 2010-095460 A | 4/2010 |
| JP | 2011-184371 A | 9/2011 |
| JP | 2012-504960 A | 3/2012 |
| JP | 2012-533303 A | 12/2012 |
| WO | 2011/081024 A1 | 7/2011 |
| WO | 2015/156339 A1 | 10/2015 |
| WO | WO 2015156339 A1 * | 10/2015 |

OTHER PUBLICATIONS

International Search Report for PCT/JP2016/061386 dated May 24, 2016.

* cited by examiner

*Primary Examiner* — Michael V Meller
(74) *Attorney, Agent, or Firm* — Sughrue Mion, PLLC

(57) ABSTRACT

Provided are an inhibitor, a prophylactic, and a therapeutic agent for rheumatoid arthritis that have no side effects and that can correct immune abnormality associated with rheumatoid arthritis. The inhibitor, the prophylactic, and the agent for rheumatoid arthritis contain a *Euglena*-derived material as an active ingredient. The inhibitor, the prophylactic and the agent are used as an antirheumatic drug for controlling the activity of rheumatoid arthritis by alleviating immune abnormality associated with rheumatoid arthritis. The inhibitor, the prophylactic, and the agent are also used for a living individual who has not been definitively diagnosed with rheumatoid arthritis. The inhibitor, the prophylactic, and the agent are continuously administered to the living individual from any point before definitive diagnosis of rheumatoid arthritis to any point after the definitive diagnosis. The *Euglena*-derived material is at least one material selected from the group including *Euglena* algae, paramylon derived from the *Euglena*, water-soluble amorphous paramylon prepared by treating the paramylon with alkali and neutralizing the treated paramylon, and emulsion paramylon prepared by ejecting a solution of the paramylon from a narrow bore nozzle at a very high pressure to cause the solution to collide with a collision surface.

1 Claim, 16 Drawing Sheets

<SITE FOR PREPARATION OF PATHOLOGICAL
SAMPLE OF A KNEE JOINT>
FIG. 9(A)
FIG. 9(B)
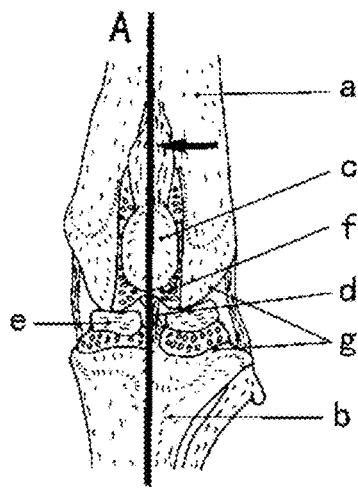
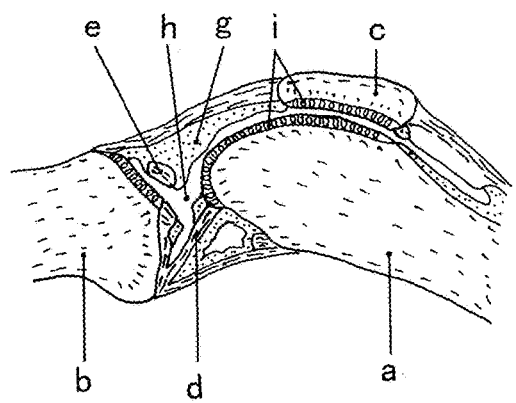

<UNTREATED GROUP>

<CONTROL GROUP>

*THE NUMERALS IN THE PHOTOGRAPHS REPRESENT RATINGS.
RATING 0: NO CHANGE, RATING 1: VERY MILD,
RATING 2: MILD, RATING 3: MODERATE,
RATING 4: SEVERE

<EUGLENA GROUP>

GRANULATION TISSUE FORMATION(1)
NEOVASCULAR VESSEL AND FIBROBLAST

*THE NUMERALS IN THE PHOTOGRAPHS REPRESENT RATINGS.
RATING 0: NO CHANGE, RATING 1: VERY MILD,
RATING 2: MILD, RATING 3: MODERATE, RATING 4: SEVERE

<PARAMYLON GROUP>

*THE NUMERALS IN THE PHOTOGRAPHS REPRESENT RATINGS.
RATING 0: NO CHANGE, RATING 1: VERY MILD,
RATING 2: MILD, RATING 3: MODERATE, RATING 4: SEVERE

<AMORPHOUS PARAMYLON GROUP>

GRANULATION TISSUE FORMATION(1)
NEOVASCULAR VESSEL AND FIBROBLAST

*THE NUMERALS IN THE PHOTOGRAPHS REPRESENT RATINGS.
RATING 0: NO CHANGE, RATING 1: VERY MILD,
RATING 2: MILD, RATING 3: MODERATE, RATING 4: SEVERE

<EMULSION PARAMYLON GROUP>

*THE NUMERALS IN THE PHOTOGRAPHS REPRESENT RATINGS.
RATING 0: NO CHANGE, RATING 1: VERY MILD,
RATING 2: MILD, RATING 3: MODERATE, RATING 4: SEVERE

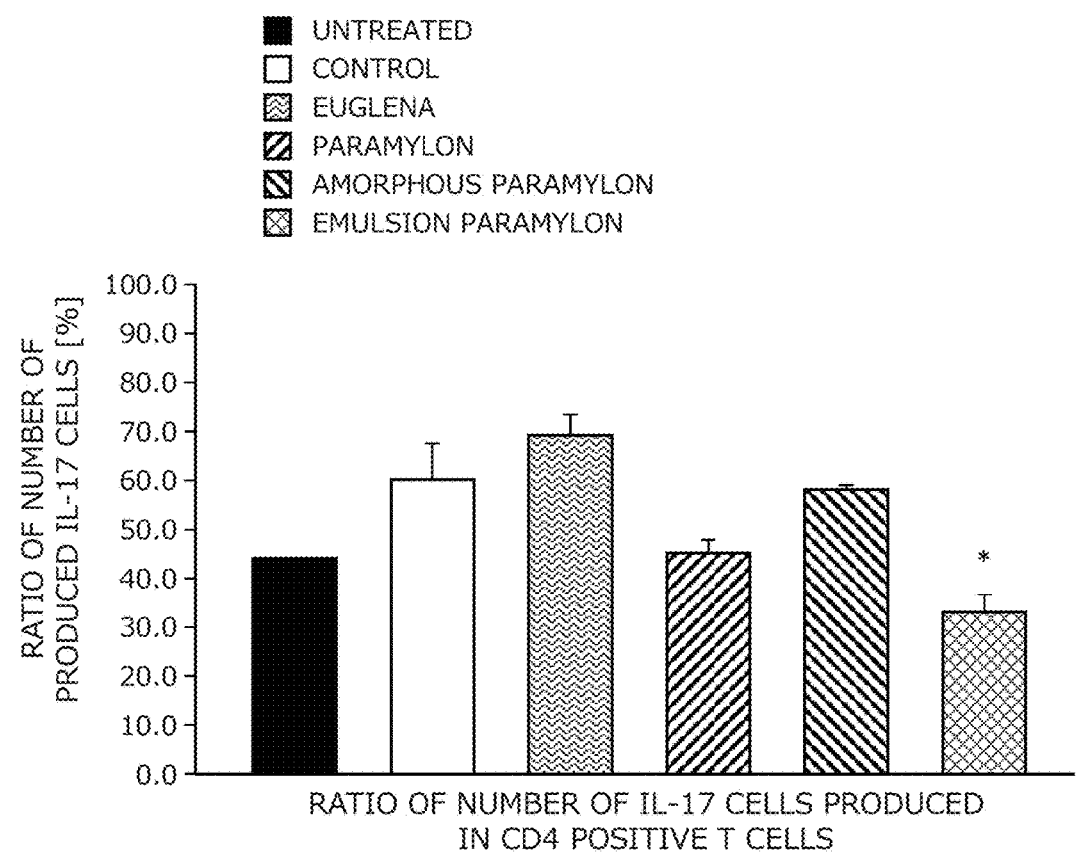

SUPPRESSIVE AGENT FOR RHEUMATOID ARTHRITIS, PROPHYLACTIC AGENT FOR RHEUMATOID ARTHRITIS, THERAPEUTIC AGENT FOR RHEUMATOID ARTHRITIS, AND FOOD FOR SUPPRESSING RHEUMATOID ARTHRITIS

CROSS REFERENCE TO RELATED APPLICATIONS

This application is a National Stage of International Application No. PCT/JP2016/061386 filed Apr. 7, 2016, claiming priority based on Japanese Patent Application No. 2015-079525 filed Apr. 8, 2015, the contents of all of which are incorporated herein by reference in their entirety.

TECHNICAL FIELD

The present invention relates to an inhibitor, a prophylactic, and a therapeutic agent for rheumatoid arthritis, and food for inhibiting rheumatoid arthritis.

BACKGROUND ART

Rheumatoid arthritis is a disorder that causes joint swelling and pain in the hands and feet, as the autoimmunity affects the joints in the hands and feet. As the disorder progresses, bone and cartilage destruction causes joint stiffness, thereby severely affecting the daily lives.

Rheumatoid arthritis had been a refractory disorder, the etiology and the pathology of which were unknown, and that could not be prevented or cured. In recent years, however, as the pathology has been elucidated, inhibition of T cells or inflammatory cytokines has been found to provide a significant amelioration. Accordingly, the use of a suitable combination of therapeutic agents has allowed for targeting, as a specific therapeutic objective, inhibition of joint destruction, even if slightly, and remission where the symptoms are controlled.

Pharmaceutical agents used in drug therapy against rheumatoid arthritis are broadly classified into non-steroidal anti-inflammatory drugs (NSAIDS), which have analgesic, antipyretic and anti-inflammatory effects and nonspecifically suppress inflammatory response; steroid drugs, which rapidly and effectively suppress inflammation due to rheumatoid arthritis and significantly improve the QOL in patients suffering from rheumatoid arthritis with active lesions; antirheumatic drugs (disease modifying antirheumatic drugs: DMARDs), which do not have the effect of suppressing inflammation itself, but alleviate immune abnormality associated with rheumatoid arthritis to control the activity of rheumatoid arthritis; and biological drugs, which are antibodies or fusion proteins developed by genetic engineering techniques in order to selectively inhibit a cytokine or the like intimately involved in the pathology of rheumatoid arthritis.

There are no pharmaceutical agents for rheumatoid arthritis, the agents having all of the effect of inducing remission of rheumatic inflammation, the effect of inhibiting the progression of joint destruction, and rapid effects. And some of the agents have strong side effects, and others of the agents have mild side effects. Thus, these pharmaceutical agents are used in complementary combination in the drug therapy.

Among the above pharmaceutical agents, antirheumatic drugs are classified into immunomodulatory drugs, which correct abnormal immune function without affecting normal immune function (for example, see Patent Literature 1), and immunosuppressive drugs, which nonspecifically suppress overall immune function (for example, Patent Literature 2), based on its mechanism of action.

CITATION LIST

Patent Literatures

PATENT LITERATURE 1: JP H8-301875A
PATENT LITERATURE 2: JP 3839836B

SUMMARY OF INVENTION

Technical Problem

However, conventional antirheumatic drugs generally have effects that significantly differ from one individual to another, and the conventional drugs may be ineffective for some cases, although the drugs are effective for other cases.

The conventional drugs also have a high incidence of a side effect and a slow onset of effect in the range of from about 2 weeks to 3 months. The antirheumatic drugs cannot be administered until rheumatoid arthritis is definitively diagnosed, due to its high incidence of a side effect. A research on the actual situation (Pfizer Japan Inc., "Research on Actual Situation of 500 Patients with Rheumatoid Arthritis", Nov. 24, 2011) reports that it took 3 months or more to make definitive diagnosis in over 50% or more of patients with rheumatoid arthritis, and it took 6 months or more from recognition of a symptom to initiation of administration of an antirheumatic drug in over 80% of the patients. It is not uncommon that it took 6-12 months or more from recognition of a symptom to onset of effect of the antirheumatic drug.

In addition, the antirheumatic drugs are initially administered at a low dose to determine the effects and the presence of a side effect, which is a factor that delays onset of the effects of the antirheumatic drugs.

Antirheumatic drugs that have little side effect and that shows little difference in effects among different cases are little known.

The present invention has been made in view of the foregoing problems, and an object of the present invention is to provide an inhibitor, a prophylactic, and a therapeutic agent for rheumatoid arthritis, and food for inhibiting rheumatoid arthritis, that have no side effects and that can correct immune abnormality associated with rheumatoid arthritis.

Another object of the present invention is to provide an inhibitor, a prophylactic, and a therapeutic agent for rheumatoid arthritis, and food for inhibiting rheumatoid arthritis, that can be administered prior to onset or diagnosis of rheumatoid arthritis.

Solution to Problem

The problems are solved by an inhibitor, a prophylactic, and a therapeutic agent for rheumatoid arthritis according to the present invention, the inhibitor, the prophylactic, and the agent containing a *Euglena*-derived material as an active ingredient.

As the inhibitor, the prophylactic, and the agent contain a *Euglena*-derived material that has the effect of inhibiting rheumatoid arthritis, as an active ingredient, they can effectively inhibit, prevent, and treat rheumatoid arthritis. As the inhibitor, the prophylactic, and the agent contain a *Euglena*-derived material that has no side effects and that is sufficiently safe to be used as food, as an active ingredient, they can be administered to individuals who are genetically or environmentally susceptible to rheumatoid arthritis, individuals who are aware of a symptom associated with rheumatoid arthritis but have not been examined or definitively diagnosed, and the like.

The inhibitor, the prophylactic, and the agent may be used as an antirheumatic drug for controlling the activity of rheumatoid arthritis by alleviating immune abnormality associated with rheumatoid arthritis.

Such configuration allows for the inhibitor, the prophylactic, and the agent to be used in combination with another steroid drug, non-steroidal anti-inflammatory drug, antirheumatic drug, or the like, in view of individual symptoms and amelioration in a patient with rheumatoid arthritis to target remission and subsequent cure of rheumatoid arthritis.

The inhibitor, the prophylactic, and the agent may also be used for a living individual who has not been definitively diagnosed with rheumatoid arthritis.

The inhibitor, the prophylactic, and the agent may be continuously administered to the living individual from any point before definitive diagnosis of rheumatoid arthritis to any point after the definitive diagnosis.

As the inhibitor, the prophylactic, and the agent can be continuously administered to the living individual from any point before definitive diagnosis of rheumatoid arthritis, they can be administered without the necessity of waiting for the definitive diagnosis, so that the activity of rheumatoid arthritis can be rapidly suppressed. It takes about three to six months, which is a period required from recognition of a symptom to definitive diagnosis according to a private study, for the inhibitor, the prophylactic, or the agent for rheumatoid arthritis according to the present invention to provide the effect of controlling the activity of rheumatoid arthritis, and thus we can target early remission and cure of rheumatoid arthritis.

The *Euglena*-derived material may be at least one material selected from the group including *Euglena* algae, paramylon derived from the *Euglena*, water-soluble amorphous paramylon prepared by treating the paramylon with alkali and neutralizing the treated paramylon, and emulsion paramylon prepared by ejecting a solution of the paramylon from a narrow bore nozzle at a very high pressure to cause the solution to collide with a collision surface.

The problems are also solved by food for inhibiting rheumatoid arthritis according to the present invention, the food containing a *Euglena*-derived material as an active ingredient and being characterized by use in prevention or amelioration of rheumatoid arthritis.

Such configuration allows for individuals who are genetically or environmentally susceptible to rheumatoid arthritis, individuals who are aware of a symptom associated with rheumatoid arthritis but have not been examined or definitively diagnosed, and the like to eat the food to benefit from the effect of preventing or ameliorating rheumatism.

Advantageous Effects of Invention

As the inhibitor, the prophylactic, the agent, and the food according to the present invention contain a *Euglena*-derived material that has the effect of inhibiting rheumatoid arthritis, as an active ingredient, they can effectively inhibit, prevent, treat, and ameliorate rheumatoid arthritis. As the inhibitor, the prophylactic, the agent, and the food contain a *Euglena*-derived material that has no side effects and that is sufficiently safe to be used in food, as an active ingredient, they can be administered to or eaten by individuals who are genetically or environmentally susceptible to rheumatoid arthritis, individuals who are aware of a symptom associated with rheumatoid arthritis but have not been examined or definitively diagnosed, and the like.

BRIEF DESCRIPTION OF DRAWINGS

FIGS. 9(A) and 9(B) illustrate a method for preparing a pathological sample of a knee joint to evaluate the tissue of the knee joint in mouse models of collagen arthritis in Test Example 2.

FIG. 16 is a graph illustrating the ratio of IL-17 cells produced in CD4 positive T cells in mouse models of collagen arthritis in Test Example 2.

DESCRIPTION OF EMBODIMENTS

Figure 1:
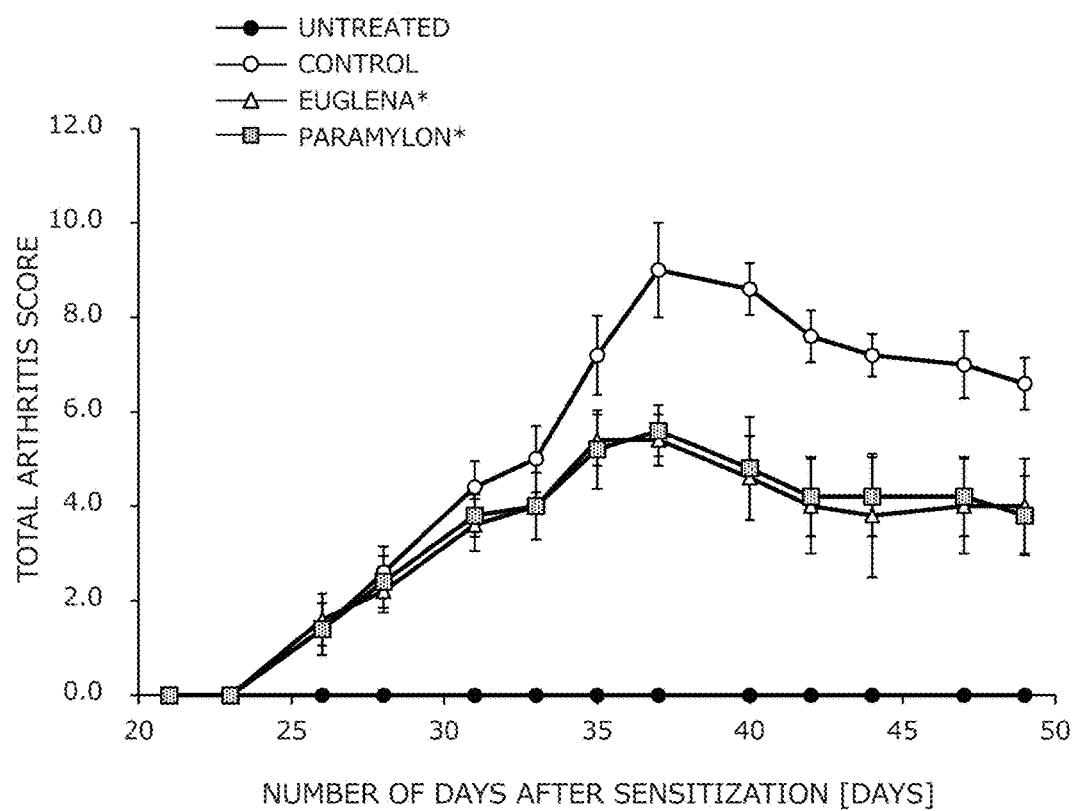
FIG. 1 is a graph illustrating arthritis scores of mouse models of collagen arthritis in Test Example 1.

Now, an inhibitor, a prophylactic, and a therapeutic agent for rheumatoid arthritis according to an embodiment of the present invention will be described with reference to FIGS. 1-16.

As used herein, "living individuals" include mammalian animals such as humans, domestic animals, and pets and any living individuals suffering from rheumatoid arthritis.

The embodiment is an inhibitor, a prophylactic, and a therapeutic agent for rheumatoid arthritis, the inhibitor, the prophylactic, and the agent containing a *Euglena*-derived material as an active ingredient.

Preferably, the *Euglena*-derived material contains paramylon, and the examples include *Euglena*, dried *Euglena* products, paramylon, paramylon powder, and processed products from paramylon. The *Euglena*-derived material may also be *Euglena* or dried *Euglena* products to which paramylon or processed products from paramylon has been added.

As used herein, "*Euglena*" include all of the microorganisms classified as genus *Euglena* in zoology and botany, varieties thereof, and variants thereof.

In zoology, the microorganisms of the genus *Euglena* belong to the suborder Euglenoidina of the order Euglenida of the class Phytomastigophorea of the class Mastigophorea of the phylum Protozoa. In botany, the microorganisms of the genus *Euglena* belong to the order Euglenales of the class Euglenophyceae of the phylum Euglenophyta.

Specific examples of the microorganisms of the genus *Euglena* include *Euglena acus*, *Euglena caudata*, *Euglena chadefaudii*, *Euglena deses*, *Euglena gracilis*, *Euglena granulata*, *Euglena intermedia*, *Euglena mutabilis*, *Euglena oxyuris*, *Euglena proxima*, *Euglena spirogyra*, *Euglena viridis*, *Euglena vermiformis*, *Euglena intermedia*, and *Euglena piride*. As *Euglena* cells, *Euglena gracilis* (*E. gracilis*) and, in particular, the strain *Euglena gracilis* (*E. gracilis*) Z can be used. The *Euglena* may also be species such as the strain SM-ZK (chloroplast deficient strain), which is a mutant of the strain *Euglena gracilis* (*E. gracilis*) Z, var. *bacillaris*, or β-1,3-glucanase derived from a genetic mutant strain such as chloroplast mutants thereof, *Euglena intermedia*, *Euglena piride*, and other *Euglena* such as, for example, *Astasia longa*.

The genus *Euglena* generally live in fresh water such as pools and ponds, and thus *Euglena* may be isolated from such water. Alternatively, any previously-isolated *Euglena* may be used.

The genus *Euglena* in the present invention encompass all mutant strains. The mutant strains encompass those produced through genetic techniques such as, for example, recombination, transduction, and transformation.

Culture for cultivating *Euglena* cells may be, for example, culture supplemented with nutrient salts such as one or more nitrogen sources, phosphorus sources, and minerals. For example, modified Cramer-Myers medium (1.0 g/L of $(NH_4)_2HPO_4$, 1.0 g/L of $KH_2PO_4$, 0.2 g/L of $MgSO_4.7H_2O$, 0.02 g/L of $CaCl_2.2H_2O$, 3 mg/L of $Fe_2(SO_2)_3.7H_2O$, 1.8 mg/L of $MnCl_2.4H_2O$, 1.5 mg/L of $CoSO_4.7H_2O$, 0.4 mg/L of $ZnSO_4.7H_2O$, 0.2 mg/L of $Na_2MoO_4. 2H_2O$, 0.02 g/L of $CuSO_4.5H_2O$, 0.1 mg/L of thiamine hydrochloride (vitamin $B_1$), cyanocobalamin (vitamin $B_{12}$), (pH 3.5)) can be used. The $(NH_4)_2HPO_4$ may be replaced by $(NH_4)_2SO_4$ or $NH_3$aq. Known Hutner medium or Koren-Hutner medium prepared according to the description in "*Euglena*—Physiology and Biochemistry (in Japanese)" (Kitaoka, S (ed.), Gakkai Shuppan Center, K.K.) may also be used.

The culture preferably has a pH of 2 or higher, preferably with an upper limit being 6 or lower, and more preferably with an upper limit being 4.5 or lower. In the culture having an acidic pH, photosynthetic microorganisms can grow better than other microorganisms, so that contamination can be inhibited.

*Euglena* cells may be cultivated using an open pond process that directly uses sunlight, or a light collection method that collects sunlight through a light collection device, the sunlight which is subsequently transmitted through fiber optics or the like to a fermenter tank where the cells are exposed to the light for photosynthesis.

*Euglena* cells may also be cultivated using, for example, a fed-batch process. *Euglena* cells may be cultivated using any liquid cultivation process such as flask cultivation, fermenter cultivation, batch cultivation, semi-batch cultivation (fed-batch cultivation), or continuous cultivation (perfusion cultivation).

*Euglena* cells can be cultivated using a known fermenter such as an open pond fermenter, a raceway fermenter, or a tubular fermenter or a laboratory fermenter such as a Sakaguchi flask, an Erlenmeyer flask, or a reagent bottle. *Euglena* utilizes $CO_2$, and thus if *Euglena* is cultivated using the Cramer-Myers medium, which is an autotrophic medium, the medium is preferably gassed with air containing 1-5% $CO_2$. It is also preferred to add about 1-5 g of ammonium phosphate per liter of the medium to sufficiently develop chloroplasts. Suitably, the cultivation is carried out generally at a temperature of from 20 to 34° C. and particularly from 28 to 30° C. *Euglena* usually enters the logarithmic growth phase in 2-3 days after the initiation of the cultivation and reach the stationary phase in about 4-5 days, depending on the cultivation conditions.

*Euglena* may be cultivated under light exposure (light cultivation) or without light exposure (dark cultivation).

*Euglena* cells may be isolated by, for example, centrifugation of the culture or simple sedimentation.

Paramylon is a polymer of about 700 glucose units polymerized through β-1,3-linkages (β-1,3-glucan) and is a reserve polysaccharide contained in *Euglena*. Paramylon particles have a flattened spheroid shape and are formed of helically entangled β-1,3-glucan chains.

Paramylon exists, as granules, in *Euglena* cells of all species and varieties, and the number, shape, and particle uniformity vary with the species.

Paramylon is only composed of glucose, and paramylon from wild type *E. gracilis* Z or chloroplast deficient mutant SM-ZK has an average degree of polymerization of about 700 glucose units.

While paramylon is insoluble in water and hot water, paramylon is soluble in dilute alkali, concentrated acid, dimethyl sulfoxide, formaldehyde, and formic acid.

Paramylon in *E. gracilis* Z and paramylon in *E. gracilis* var. *bacillaris* SM-L1 have average densities of 1.53 and 1.63, respectively.

X-ray analysis using a powder pattern technique shows that paramylon assumes a gentle helical configuration of three linear β-glucan chains twined together like a right-hand rope. Some of the glucan molecules aggregate to form each paramylon granule. Paramylon granules have a large number of crystal structures, which make up about 90%, and paramylon is a compound having the highest crystal structure ratio among polysaccharides. Paramylon is also less likely to contain water ("*Euglena*—Physiology and Biochemistry (in Japanese)" (Kitaoka, S (ed.), Gakkai Shuppan Center, K.K.)).

Paramylon particles are isolated from cultivated *Euglena* by any suitable technique and are purified into fine particles, which are usually provided as powder.

For example, paramylon particles can be obtained by (1) cultivation of *Euglena* cells in any suitable medium, (2) separation of the *Euglena* cells from the medium, (3) isolation of paramylon from the separated *Euglena* cells, (4)

purification of the isolated paramylon, and optionally, (5) cooling and subsequent freeze-drying.

Paramylon may be isolated using, for example, a nonionic or anionic surfactant of a type that is mostly biodegradable. In practice, paramylon can be purified simultaneously with its isolation.

Isolation and purification of paramylon from *Euglena* are well known and described in, for example, E. Ziegler, "Die naturlichen and kunstlichen Aromen" Heidelberg, Germany, 1982, Chapter 4.3 "Gefriertrocken", DE 43 28 329, and JP 2003-529538A.

Examples of the processed product from paramylon include amorphous paramylon and emulsion paramylon.

Amorphous paramylon is produced by amorphization of crystalline paramylon derived from *Euglena*.

Amorphous paramylon used in the embodiment has a relative crystallinity of 1-20% relative to that of crystalline paramylon produced from *Euglena* by a known method.

The relative crystallinity is determined by the method described in JP 5612875B.

In particular, amorphous paramylon and paramylon are individually ground in a pulverizer (MM400 ball mill from Retsh) at 20 oscillations per second for 5 minutes, and then scanned with an X-ray diffractometer (H'PertPRO from Spectris Co., Ltd.) at a tube voltage of 45 KV, a tube current of 40 mA, and 2θ in the range of from 5° to 30° to obtain diffraction peaks Pc for the paramylon and Pa for the amorphous paramylon at 2θ of about 20°.

The Pc and Pa values are used to calculate the relative crystallinity of amorphous paramylon as follows:

Relative Crystallinity of Amorphous Paramylon=$Pa/Pc\times100(\%)$

According to the method described in JP 5612875B, amorphous paramylon used in the embodiment is prepared by treating crystalline paramylon powder with alkali, neutralizing the treated product with acid, washing the product, processing the washed product through a water removing step, and then drying the product.

Processed products from paramylon additionally include water-soluble paramylon, sulfated paramylon that are obtained by chemically or physically treating paramylon by various other known methods, and paramylon derivatives.

The emulsion paramylon is named after its production method and physical properties that are similar to those of emulsion. The emulsion paramylon is obtained by adding water to paramylon to produce fluid and ejecting the fluid from a narrow bore nozzle at a very high pressure to cause the fluid to collide with a collision surface. The emulsion paramylon is a processed paramylon swelled by binding to over 4 times as much water as paramylon.

The emulsion paramylon can be obtained by adding a water-soluble solvent to solid such as powder to form a slurry, ejecting the slurry from a narrow bore nozzle at a very high pressure to cause the slurry to collide with a collision surface one or more times using a known device for modifying a physical property (for example, a device as described in JP 2011-88108A and JP H06-47264A) at a nozzle-outlet pressure of 245 MPa.

The emulsion paramylon has a median size as a particle size of 7 μm or more, which is 5 times or more of the size of paramylon, as measured on a laser diffraction/scattering particle size distribution analyzer. Observation under a photoelectron microscope indicates that the particles are in contact with adjacent particles and are swelled by binding to over 4 times as much water as paramylon.

While the slurry produced by combining a paramylon raw material and water is flowable fluid, the emulsion paramylon, which is a dispersion of paramylon in water molecules, has increased viscosity, which causes the emulsion paramylon to stick to hands, and elasticity, which provide a glue-like touch.

Although in this specification, the resultant processed paramylon is named emulsion paramylon after its processing method and physical properties, it is not clear whether the processed paramylon is emulsified. The paramylon is just swelled by binding to water.

The inhibitor, the prophylactic, and the agent for rheumatoid arthritis of the embodiment can be used in a composition such as a pharmaceutical composition, a food composition, or a cosmetic composition that contains the inhibitor, the prophylactic, and the agent for rheumatoid arthritis.

The agent for rheumatoid arthritis of the embodiment is administered, as an antirheumatic drug, to patients definitively diagnosed with rheumatoid arthritis.

The inhibitor and the prophylactic for rheumatoid arthritis of the embodiment are configured as a a pharmaceutical composition, health food, or the like, and prophylactically administered to individuals who are aware of a symptom associated with rheumatoid arthritis, individuals who are genetically or environmentally susceptible to rheumatoid arthritis, and the like.

As the *Euglena*-derived material can be eaten as food and has no side effects, the *Euglena*-derived material can be administered even before definitive diagnosis of rheumatoid arthritis. And the *Euglena*-derived material can be continuously administered from any point before the definitive diagnosis to any point after the definitive diagnosis such as, for example, a point where the remission is achieved, a point where the disease is cured, or a point where the material is switched to another therapeutic agent for rheumatoid arthritis such as another antirheumatic drug.

The inhibitor and the prophylactic for rheumatoid arthritis of the embodiment are administered to patients with rheumatoid arthritis who have achieved remission by treatment, for the purpose of inhibiting relapse of the symptoms.

As used herein, "remission" refers to a state in which the conditions of rheumatoid arthritis are controlled by treatment and in which symptoms of rheumatoid arthritis have disappeared and a state before "cure", which means a state in which durable remission has been achieved.

<<Pharmaceutical Composition>>

In the field of medicament, a pharmaceutical composition that has the effect of inhibiting, preventing, and treating rheumatism can be provided by formulating a *Euglena*-derived material in an amount sufficient to effectively provide the effect of inhibiting, preventing, and treating rheumatism with a pharmaceutically acceptable carrier and a pharmaceutically acceptable additive. The pharmaceutical composition may be a pharmaceutical drug or a quasi-drug.

The pharmaceutical composition may be used internally or externally. In particular, the pharmaceutical composition may be used in a dosage form such as an oral agent; an injectable such as an intravenous injectable, a subcutaneous injectable, an intradermal injectable, an intramuscular injectable, and/or an intraperitoneal injectable; a transmucosal agent; or a transdermal agent.

The dosage form of the pharmaceutical composition can be appropriately determined depending on the administration mode, and the examples include solid formulations such as tablets, granules, capsules, and powders; and fluid formulations such as solutions and suspensions; and semi-solid formulations such as ointments and gels.

<<Food Composition>>

In the field of food, a food composition that has the effect of inhibiting, preventing, and treating rheumatism can be provided by formulating various food with a *Euglena*-derived material as a food material in an amount sufficient to exhibit suppressive, prophylactic, or therapeutic effects for rheumatism in a living individual. In other words, the present invention can provide, in the field of food, food compositions having an indication that they are useful for the inhibition, prevention, or treatment of rheumatism. Examples of these food compositions include general food, food for specified health use, nutritional supplement food, functional food, food for inpatients, and supplements. The compositions may also be used as a food additive.

As used herein, "food for specified health use" refers to food that contains a healthy component having an effect on a physiological function or the like and that has gained approval from the Secretary General of the Japanese Consumer Affairs Agency to indicate that the food is suitable for specified health use. In the present invention, "food for specified health use" is provided with an indication that the food attenuates the progression of renal failure, prevents and ameliorates renal failure, prevents and ameliorates uremia, inhibits production of indoxyl sulfate in a living individual, and the like for specified health use.

"Food with nutrient function claims" refers to food that is used to supplement the diet with a nutrient component (vitamin or mineral) and that is provided with an indication of the function of the nutrient component. To sell a food product as food with nutrient function claims, the food product must satisfy the standard for the minimum and maximum levels of the nutrient component per daily portion usually consumed and must be labelled with not only a nutrient function, but also warning.

"Food with function claims" refers to food that is labelled with a function based on scientific evidence under the responsibility of an entity. Prior to marketing the food product, the entity must provide information or the like on evidences for safety and function to the Secretary General of the Japanese Consumer Affairs Agency.

Examples of the food compositions can include seasoning, processed meat products, processed agricultural products, drinks (such as soft drinks, alcoholic drinks, carbonated drinks, milk drinks, fruit drinks, teas, coffee, and nourishing drinks), powdered drinks (such as powdered juice and powdered soup), concentrated drinks, confectionery (such as candies, cookies, crackers, gums, gummi candies, and chocolates), bread, and cereals. In the case of food for specified health use, nutritional supplement food, functional food, or the like, the compositions may each be in the form of capsules, troches, syrup, granules, powder, or the like.

EXAMPLES

Now, the present invention will be described in more detail with reference to specific examples, although the technical scope of the present invention is not limited to the following examples.

Example 1

*Euglena gracilis* powder (from *Euglena* Co., Ltd.) was used as *Euglena* of Example 1.

Example 2

Crystalline paramylon powder was prepared in the following manner.

The *Euglena gracilis* powder of Example 1 (from *Euglena* Co., Ltd.) was added to distilled water and stirred at room temperature for 2 days. The resultant was ultrasonically treated to destroy the cell membranes, and crude paramylon particles were collected by centrifugation. The collected paramylon particles were dispersed in a 1% aqueous solution of sodium dodecyl sulfate and treated at 95° C. for 2 hours. The paramylon particles were again collected by centrifugation, and the collected paramylon particles were dispersed in a 0.1% aqueous solution of sodium dodecyl sulfate and treated at 50° C. for 30 minutes. Lipids and proteins were removed by those operations. Then, the remainder was washed with acetone and ether and dried at 50° C. to give purified paramylon particles.

1 g of the prepared paramylon was enclosed in a known capsule to prepare paramylon of Example 2.

Example 3

The paramylon prepared in Example 2 was used to prepare amorphous paramylon in accordance with the method described in JP 5612875B.

Specifically, the crystalline paramylon powder prepared in Example 2 was added to and dissolved in 1 N aqueous sodium hydroxide at a concentration of 5% (w/v) and stirred for 1-2 hours with a stirrer for alkali treatment. Then, 1 N hydrochloric acid was added dropwise to the solution of the paramylon powder in the 1 N aqueous sodium hydroxide to neutralize the solution. After centrifugation, the supernatant was removed, and the precipitate was washed with distilled water. After these operations were repeated, the precipitated gel was collected. After freezing, the gel was freeze-dried using a lyophilizer to give amorphous paramylon of Example 3.

Example 4

The paramylon prepared in Example 2 was used to prepare emulsion paramylon in the following manner.

Ion-exchanged water was added to crystalline paramylon powder (from *Euglena* Co., Ltd.) to give a paramylon slurry having a paramylon concentration of 10 wt %.

A liquid medium in a wet pulverizer (Star Burst 18 KW, Mid-Scale, manufactured by Sugino Machine Ltd., Oblique Collision Chamber) was exchanged for ion-exchanged water. The nozzle of the pulverizer is pressurized, and the paramylon slurry is fed into the pulverizer. The initially discharged liquid was discarded as the dead volume in the pulverizer. Then, oblique jet collision was produced by ejecting jets of the paramylon slurry from a pair of nozzles opposed to each other at an angle to cause the slurry to collide with each other. The treated slurry was collected from the outflow channel, which was regarded as 1 pass. The treatment pressure was 245 MPa, the amount of slurry treated was 240 mL, and the diameter of the nozzles was 0.17 mm.

The above treatments were repeated 3 times (3 passes) to give emulsion paramylon of Example 4.

The emulsion paramylon of Example 4 was not separated from the ion-exchanged water added in preparation of the slurry and was swelled by binding to water.

Test Example 1: Assessment 1 Using Mouse Models of Collagen Arthritis

In this test example, the effect of the test materials in Examples 1 and 2 on rheumatoid arthritis was assessed in mouse models of collagen arthritis.

Chicken type II collagen (SIGMA) was dissolved in 0.01 M aqueous acetic acid to a concentration of 2 mg/mL. Then, an equal volume of Freund's complete adjuvant (Difco) was added to the resultant solution to prepare an emulsion (1 mg/mL of collagen), which was intradermally administered into the base of the tail of the mice in an amount of 0.1 mL (0.1 mg of collagen) under isoflurane inhalation anesthesia to sensitize the mice to the collagen. After 3 weeks, the same administration was carried out to boost the mice. And untreated animals were not sensitized and boosted.

The mice were classified into an untreated group, a control group, a *Euglena* group, and a paramylon group (n=5 in each of the groups). The test materials in Examples 1 and 2 were admixed with CE-2 solid diet (CLEA Japan, Inc.), respectively, at a concentration of 2% and were given to the mice of the *Euglena* group and the paramylon group orally ad libitum every day from day 5 after the boosting.

Determination of Arthritis Scores

From the day of sensitization to the collagen (hereinafter referred to as "sensitization day"), arthritis symptoms in the four limbs were scored by visual inspection, and the total scores for the four limbs were calculated.

The scoring was conducted three times per week (Mondays, Wednesdays, and Fridays) according to arthritis scoring criteria in Table 1 with the reference to scoring by Kakimoto et al. (Shinsei Kagaku Jikken Koza 12, Bunshi Mennekigaku II (in Japanese), Tokyo Kagaku Dojin, 360-372, 1989), and the total scores for the four limbs were calculated.

TABLE 1

| Arthritis Scores | |
|---|---|
| Score | Symptoms |
| 0 | No symptoms |
| 1 | Mild redness and swelling of a small joint of a finger or the like |
| 2 | Redness and swelling of 2 or more small joints or a large joint |
| 3 | Redness and swelling of a limb |
| 4 | Intense redness and swelling of an overall limb |

The scores per limb are 0-4, and thus the lower limit of the total scores for the four limbs is 0 (in the case where no symptoms are observed on all four limbs), while the upper limit is 16 (in the case where intense redness and swelling are observed on whole of all four limbs).

The results of the arthritis scores are illustrated in FIG. 1.

At the final scoring day, the *Euglena* group and the paramylon group exhibited a significantly lower score ($p<0.05$) compared with the control group, confirming that continuous administration of the test materials inhibits the symptoms of arthritis.

While the control group had an average score of 8 (2 per limb) at some of the time points, the *Euglena* group and the paramylon group had a decreased average score of less than 6 (less than 1.5 per limb) over the entire measurement period. Especially, between day 35 and the final day (day 49), the *Euglena* group had an average score of 4 (1 per limb) or less, and the paramylon group had an average score of 4.2 (1.05 per limb) or less, indicating that only mild redness and swelling are observed as the symptoms of arthritis.

Measurement of Cytokines

After 7 weeks from the sensitization day, the animals were sacrificed by exsanguinations. The inguinal lymph nodes (in all of the groups except for the untreated group) and then knee joints (both sides in all of the groups) were removed.

With regard to the inguinal lymph nodes, the separated lymphocytes were divided into three equal portions and individually cultured in medium supplemented with chicken type II collagen (SIGMA). After about 48 hours from the initiation of the cultivation, the culture supernatant was collected, and the levels of cytokines (IL-6, IL-17A, and IFN-γ) secreted in the culture supernatant were measured by multiplex suspension array.

Figure 2:
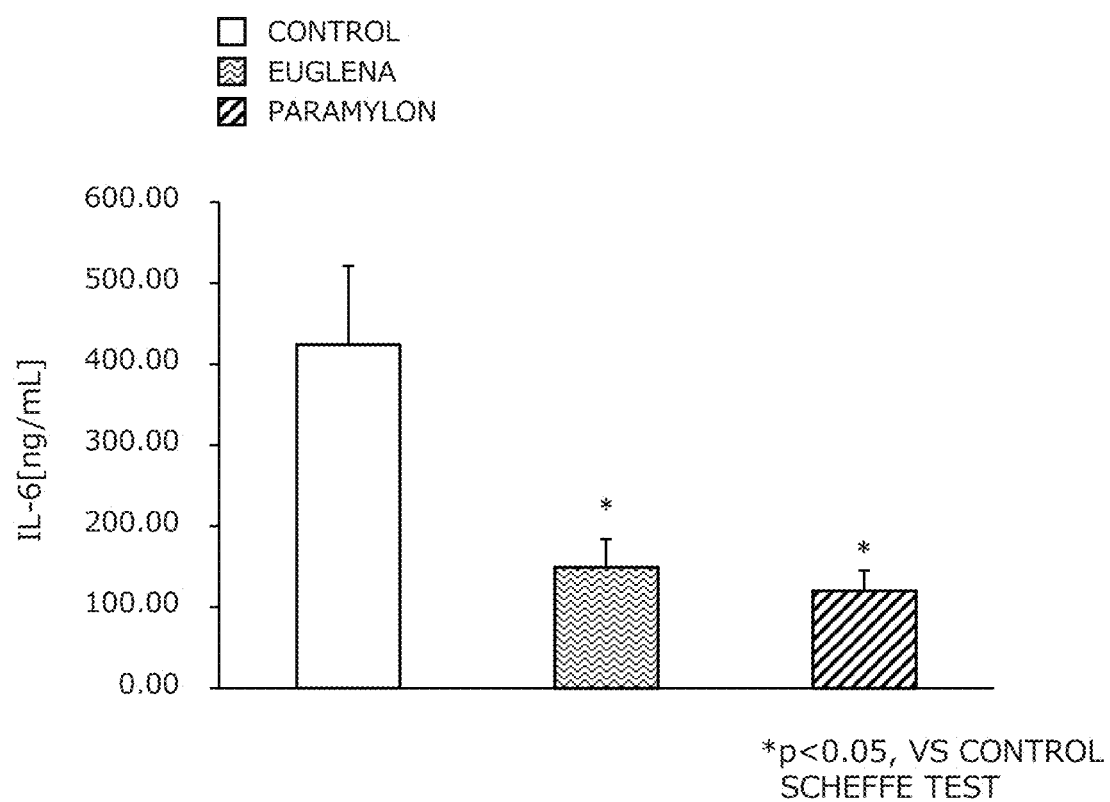
FIG. 2 is a graph illustrating measurements of cytokines (IL-6) in mouse models of collagen arthritis in Test Example 1.
Figure 3:
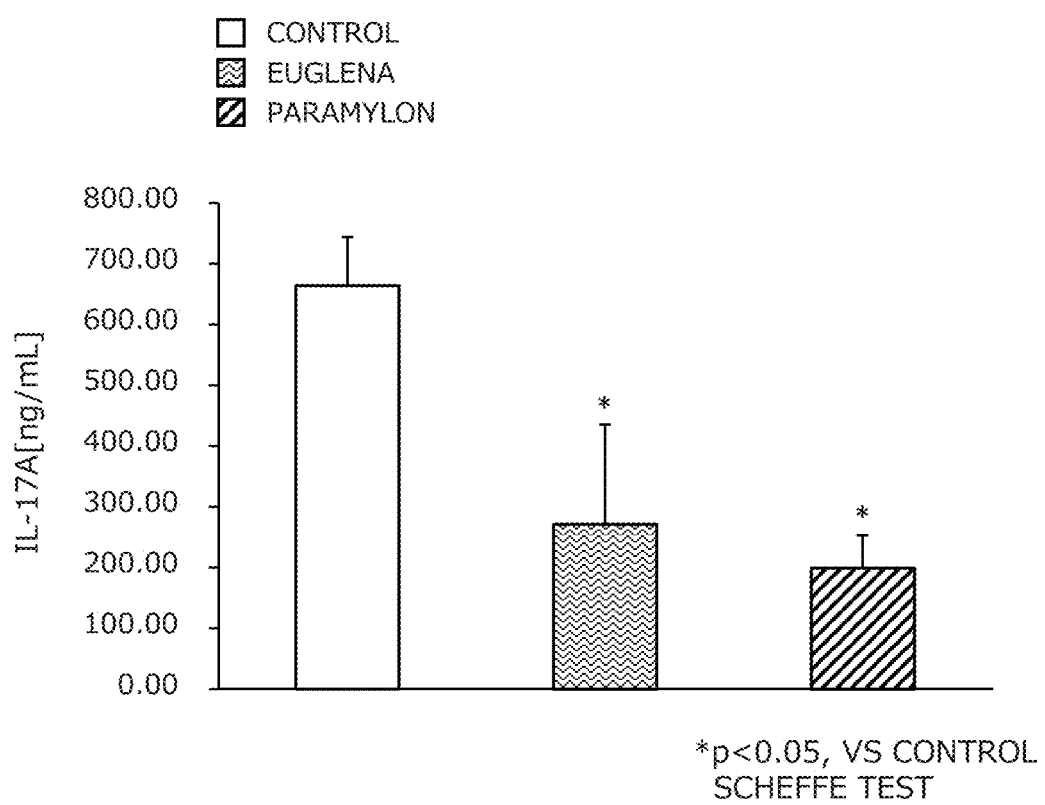
FIG. 3 is a graph illustrating measurements of cytokines (IL-17A) in mouse models of collagen arthritis in Test Example 1.
Figure 4:
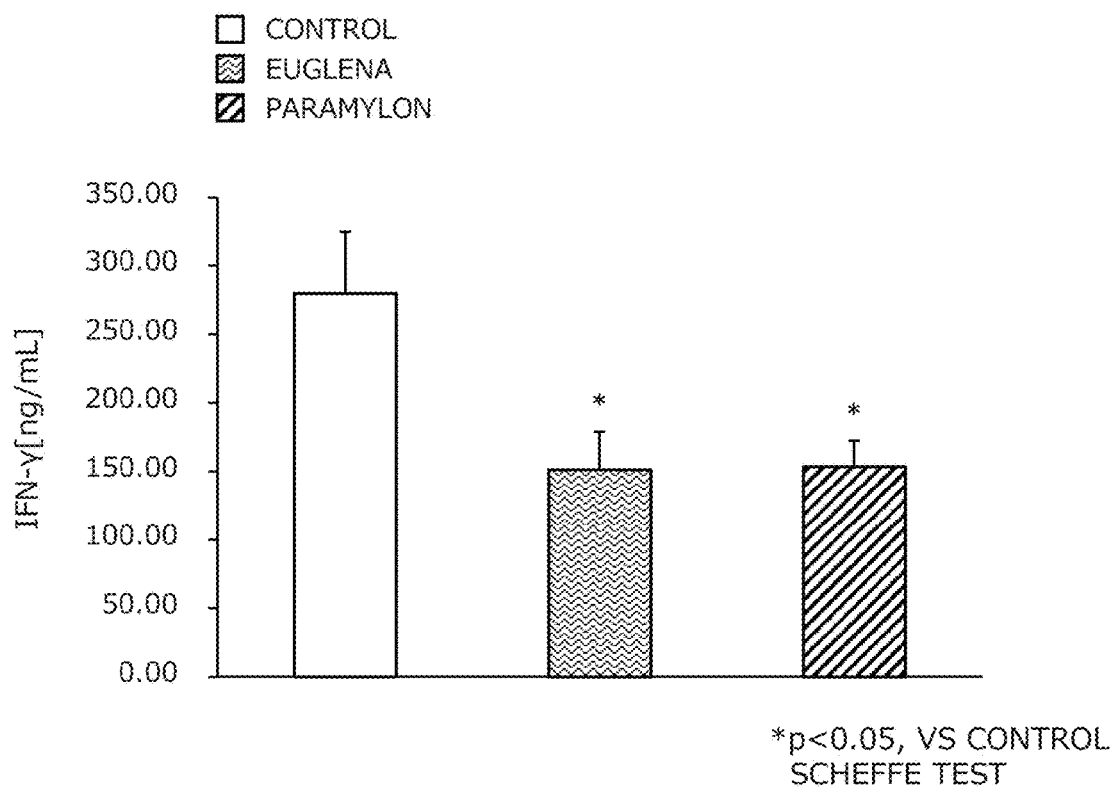
FIG. 4 is a graph illustrating measurements of cytokines (IFN-γ) in mouse models of collagen arthritis in Test Example 1.

The results are illustrated in FIGS. 2-4.

As illustrated in FIGS. 2-4, both of the *Euglena* group and the paramylon group exhibited significantly lower levels of IL-6, IL-17A, and IFN-γ cytokines compared with the control group ($p<0.05$).

Test Example 2: Assessment 2 Using Mouse Models of Collagen Arthritis

In this test example, the effect of the test materials in Examples 3 and 4 on rheumatoid arthritis was assessed in mouse models of collagen arthritis, in addition to the test materials in Examples 1 and 2, the materials being assessed in the above Test Example 1.

Except that mice were classified into an untreated group, a control group, a *Euglena* group, a paramylon group, an amorphous paramylon group, and an emulsion paramylon group (n=5 in each of the groups), the same mice as in Test Example 1 were used, and the mice in each of the groups were sensitized to the collagen and fed in the same manner as in Test Example 1.

In particular, mice (DBA/1J Jms Slc (SPF), 6 week old male, Japan SLC, Inc.) were used as the test animals.

Chicken type II collagen (SIGMA) was dissolved in 0.01 M aqueous acetic acid to a concentration of 2 mg/mL. Then, an equal volume of Freund's complete adjuvant (Difco) was added to the resultant solution to prepare an emulsion (1 mg/mL of collagen), which was intradermally administered into the base of the tail of the mice in an amount of 0.1 mL (0.1 mg of collagen) under isoflurane inhalation anesthesia to sensitize the mice to the collagen. After 3 weeks, the same administration was carried out to boost the mice. And untreated animals were not sensitized and boosted.

The mice were classified into an untreated group, a control group, a *Euglena* group, a paramylon group, an amorphous paramylon group, and an emulsion paramylon group (n=5 in each of the groups). The test materials in Examples 1-4 were admixed with CE-2 solid diet (CLEA Japan, Inc.), respectively, at a concentration of 2% and were given to the mice of the *Euglena* group, the paramylon group, the amorphous paramylon group, and the emulsion paramylon group orally ad libitum every day from day 5 after the boosting.

Determination of Arthritis Scores

From the day of sensitization to the collagen (hereinafter referred to as "sensitization day"), arthritis symptoms in the four limbs were scored by visual inspection, and the total scores for the four limbs were calculated in the same manner as in Test Example 1.

Figure 5:
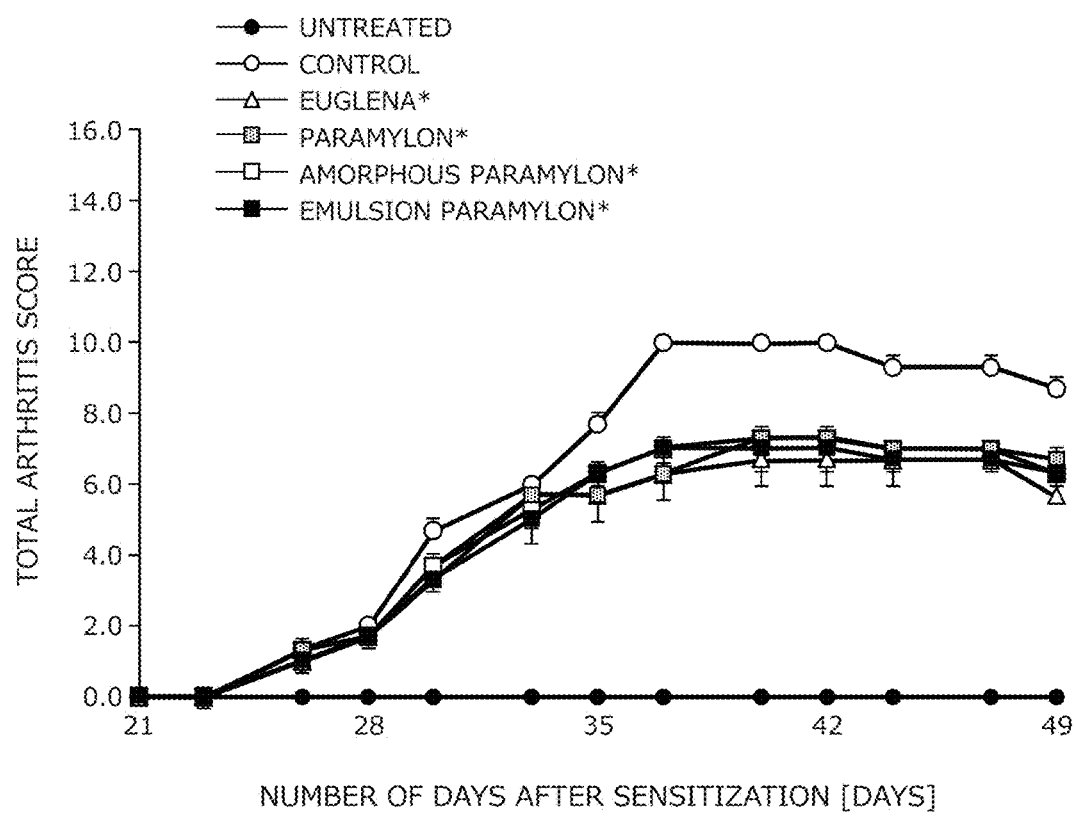
FIG. 5 is a graph illustrating arthritis scores of mouse models of collagen arthritis in Test Example 2.

The results of the arthritis scores are illustrated in FIG. 5.

At the final scoring day, all of the *Euglena* group, the paramylon group, the amorphous paramylon group, and the emulsion paramylon group exhibited a significantly lower score compared with the control group, confirming that continuous administration of the test materials inhibits the symptoms of arthritis.

Measurement of Anti-Collagen IgG

After 7 weeks from the sensitization day, the animals were subjected to a laparotomy under isoflurane inhalation anesthesia to collect the blood from the abdominal vena cava. The resultant blood was centrifuged to separate the serum, and collagen IgG in the serum was quantified (by ELISA).

Figure 6:
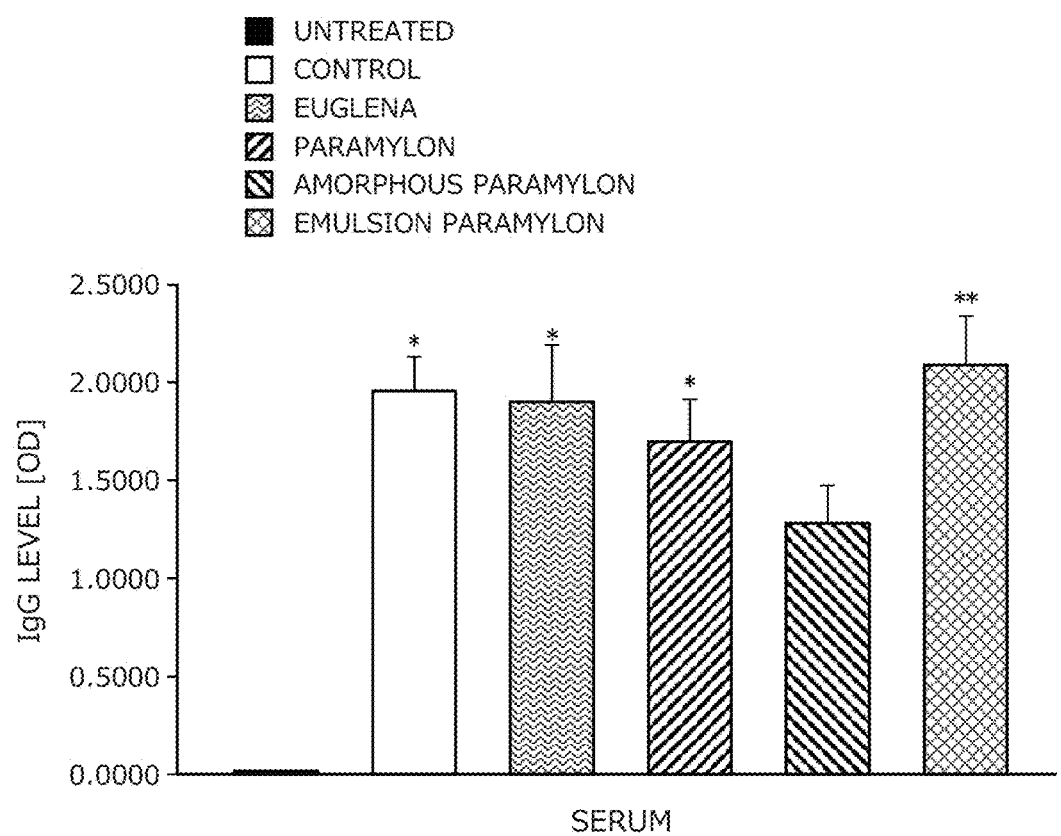
FIG. 6 is a graph illustrating measurements of anti-collagen IgG in mouse models of collagen arthritis in Test Example 2.

The measurements of the anti-collagen IgG are illustrated in FIG. 6.

The *Euglena* group, the paramylon group, the amorphous paramylon group, and the emulsion paramylon group exhibited a level similar to the level in the control group, confirming that collagen arthritis could be induced in the groups. In other words, it could be confirmed that the anti-collagen arthritis model test system was functioning effectively.

Measurement of Cytokines

The animals that had been subjected to blood collection after 7 weeks from the sensitization day were sacrificed by exsanguinations after the collection. The inguinal lymph nodes (in all of the groups except for the untreated group) and then knee joints (both sides in all of the groups) were removed.

With regard to the inguinal lymph nodes, the separated lymphocytes were divided into three equal portions and individually cultured in medium supplemented with anti-CD3 antibodies. After about 48 hours from the initiation of the cultivation, the culture supernatant was collected, and the levels of cytokines (IL-17A and IFN-$\gamma$) secreted in the culture supernatant were measured by multiplex suspension array.

Figure 7:
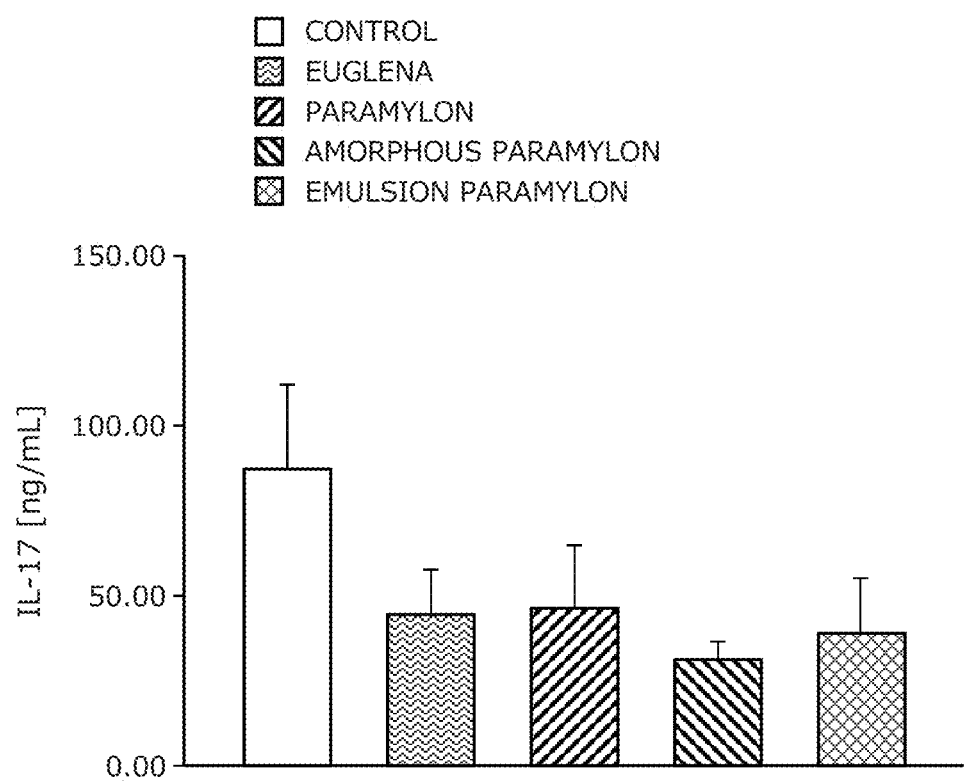
FIG. 7 is a graph illustrating measurements of cytokines (IL-17) in mouse models of collagen arthritis in Test Example 2.
Figure 8:
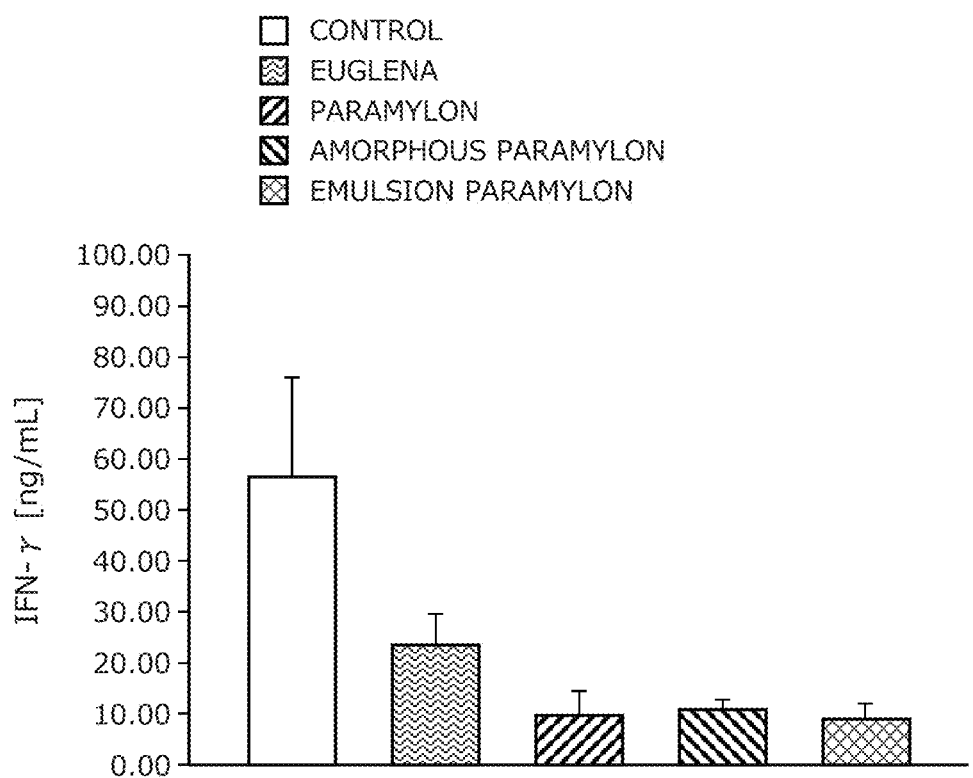
FIG. 8 is a graph illustrating measurements of cytokines (IFN-γ) in mouse models of collagen arthritis in Test Example 2.

The results are illustrated in FIG. 7 and FIG. 8.

All of the *Euglena* group, the paramylon group, the amorphous paramylon group, and the emulsion paramylon group exhibited lower levels of IL-17A and IFN-$\gamma$ cytokines compared with the control group.

Observation of Joint Tissues

The removed left-knee joints were fixed in 10% neutral buffered formalin. After decalcification in a 10% formic acid-formalin solution, the joints were cut along the line A in the trochlear groove of the femur as illustrated in (A) of FIG. 9. Paraffin sections were cut and stained with HE.

The knee joint tissue was rated according to the following criteria: the synovial membrane tissue was rated for edema, inflammatory cell infiltration, synoviocyte proliferation, granulation tissue formation, fibrosis, and exudate in the joint cavity, and the tissue in the trochlear groove of the femur was rated for pannus formation, destruction of the joint cartilage (degeneration and fibrosis), bone destruction (absorption), and osteophyte formation (reactive osteoid formation) on a scale of from 0 to 4 with 0 representing no change, 1 representing very mild, 2 representing mild, 3 representing moderate, and 4 representing severe.

The animals that had a similar average total score for the four limbs were selected as the representatives of each of the groups. Two representatives were selected from the untreated group and the control group, while three representatives were selected from the test material groups.

The results are illustrated in Table 2 and Table 3.

TABLE 2

| | | Gender Male Group | | | | | | | | | | | | |
|---|---|---|---|---|---|---|---|---|---|---|---|---|---|---|
| | | Untreated | | | | Control | | | | Euglena | | | | |
| | | Dose (%, Diet Admixture) | | | | | | | | | | | | |
| | | 0 | | | | 0 | | | | 2 | | | | |
| | | Number of Animals | | | | | | | | | | | | |
| | | 2 | | | | 2 | | | | 3 | | | | |
| Organ/ | | Extent (Rating) | | | | | | | | | | | | |
| Tissue | Founding | 0 | 1 | 2 | 3 | 0 | 1 | 2 | 3 | 0 | 1 | 2 | 3 | |
| Synovial | Edema | 2 | | | | | 1 | 1 | | | | 3 | | |
| Membrane | Inflammatory Cell Infiltration | 2 | | | | | 1 | | 1 | | | 3 | | |
| | Synoviocyte Proliferation | 2 | | | | | 1 | 1 | | | | 3 | | |
| | Granulation Tissue Formation | 2 | | | | | | 2 | | | | 2 | 1 | |
| | Fibrosis | 2 | | | | | 1 | 1 | | | | 3 | | |
| | Exudate in Joint Cavity | 2 | | | | | 1 | | 1 | | | 3 | | |
| Trochlear | Pannus Formation | 2 | | | | | 1 | 1 | | | | 3 | | |
| Groove of | Destruction of Joint Cartilage | 2 | | | | | 1 | 1 | | | | 3 | | |
| Femur | (Degeneration and Fibrosis) | | | | | | | | | | | | | |
| | Bone Destruction (Absorption) | 2 | | | | | | 2 | | | | 3 | | |
| | Osteophyte Formation | 2 | | | | | | 2 | | | | 3 | | |
| | (Reactive Osteoid Formation) | | | | | | | | | | | | | |

Histopathological Evaluation (Rating)
0: No Significant Change,
1: Very Mild,
2: Mild,
3: Moderate

TABLE 3

| Organ/ Tissue | Founding | Gender Male Group | | | | | | | | | | | |
|---|---|---|---|---|---|---|---|---|---|---|---|---|---|
| | | Paramylon | | | | Amorphous Paramylon | | | | Emulsion Paramylon | | | |
| | | Dose (%, Diet Admixture) | | | | | | | | | | | |
| | | 2 | | | | 2 | | | | 2 | | | |
| | | Number of Animals | | | | | | | | | | | |
| | | 3 | | | | 3 | | | | 3 | | | |
| | | Extent (Rating) | | | | | | | | | | | |
| | | 0 | 1 | 2 | 3 | 0 | 1 | 2 | 3 | 0 | 1 | 2 | 3 |
| Synovial Membrane | Edema | 3 | | | | 3 | | | | 2 | 1 | | |
| | Inflammatory Cell Infiltration | 2 | 1 | | | 3 | | | | | 2 | 1 | |
| | Synoviocyte Proliferation | 1 | 2 | | | 3 | | | | | 1 | 1 | 1 |
| | Granulation Tissue Formation | 2 | 1 | | | 2 | 1 | | | | 2 | 1 | |
| | Fibrosis | 1 | 1 | 1 | | 3 | | | | | 3 | | |
| | Exudate in Joint Cavity | 3 | | | | 3 | | | | 3 | | | |
| Trochlear Groove of Femur | Pannus Formation | 2 | 1 | | | 3 | | | | 2 | 1 | | |
| | Destruction of Joint Cartilage (Degeneration and Fibrosis) | 1 | 1 | 1 | | 3 | | | | 2 | 1 | | |
| | Bone Destruction (Absorption) | 3 | | | | 3 | | | | 3 | | | |
| | Osteophyte Formation (Reactive Osteoid Formation) | 3 | | | | 3 | | | | 3 | | | |

Histopathological Evaluation (Rating)
0: No Significant Change,
1: Very Mild,
2: Mild,
3: Moderate The photographs of pathological samples of the tissue of the left knee joints of the representatives of each of the groups are illustrated in FIGS. 10(A)-15(B).

Figure 10A:
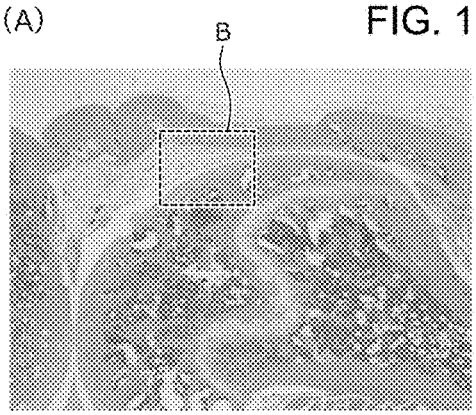
FIGS. 10(A) and 10(B) are photographs of the pathological sample of the tissue of the left knee joint of a mouse model of collagen arthritis of an untreated group in Test Example 2.
Figure 10B:
Figure 11A:
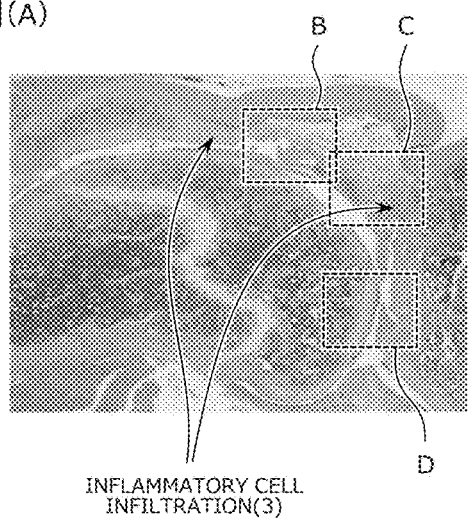
FIGS. 11(A), 11(B), 11(C) and 11(D) are photographs of the pathological sample of the tissue of the left knee joint of a mouse model of collagen arthritis of a control group in Test Example 2.
Figure 11B:
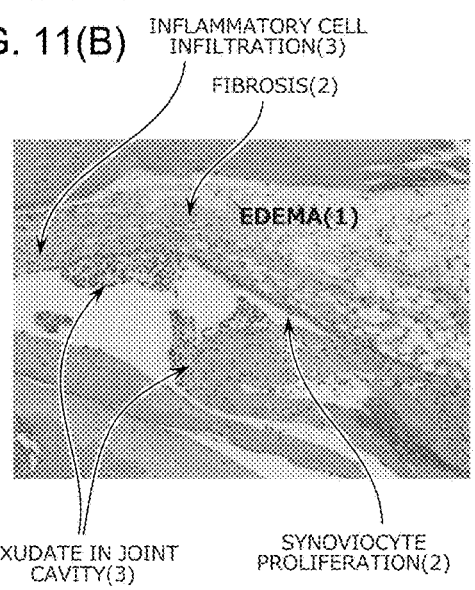
Figure 11C:
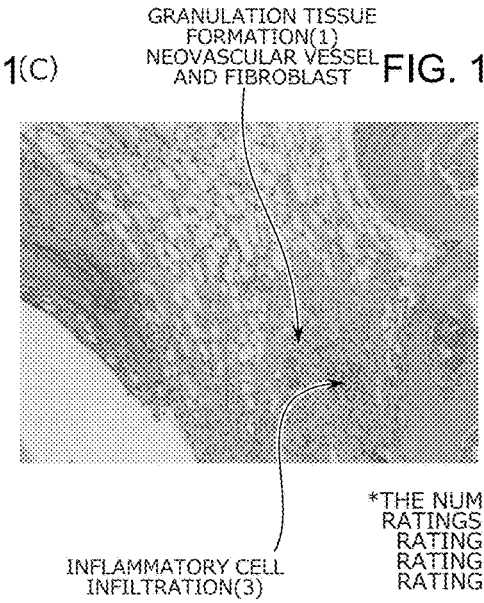
Figure 11D:
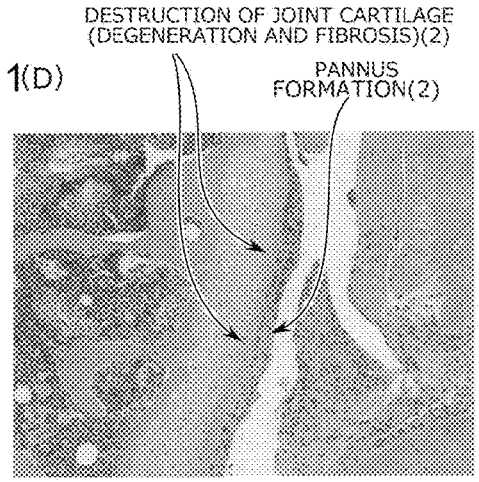

In the untreated group, as illustrated in FIGS. 10(A) and 10(B), there were no findings that might be attributed to arthritis in the synovial membranes and the trochlear grooves of the femurs.

In the control group illustrated in FIGS. 11(A), 11(B), 11(C) and 11(D), the synovial membranes had edema, inflammation, granulation tissue formation, fibrosis, and exudates rated as very mild (rating 1) to moderate (rating 3). And the trochlear grooves of the femurs had pannus formation and cartilage destruction rated as mild (rating 2).

Figure 12A:
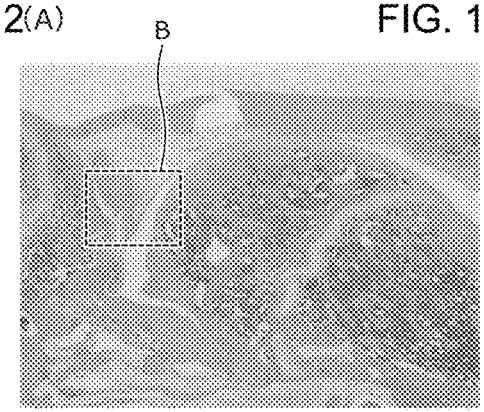
FIGS. 12(A) and 12(B) are photographs of the pathological sample of the tissue of the left knee joint of a mouse model of collagen arthritis of a *Euglena* group in Test Example 2.
Figure 12B:
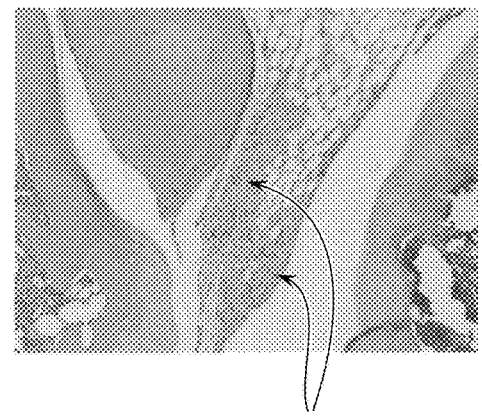
Figure 14A:
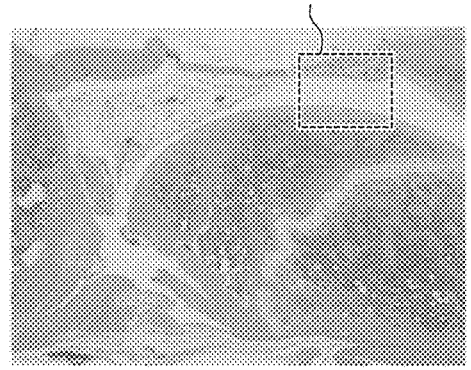
FIGS. 14(A) and 14(B) are photographs of the pathological sample of the tissue of the left knee joint of a mouse model of collagen arthritis of an amorphous paramylon group in Test Example 2.
Figure 14B:
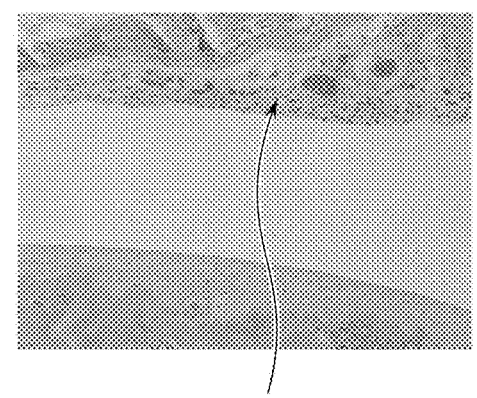

In the *Euglena* group illustrated in FIGS. 12(A) and 12(B) and the amorphous paramylon group illustrated in FIGS. 14(A) and 14(B), no findings were observed except that the synovial membranes had granulation tissue formation rated as very mild (rating 1).

Figure 13A:
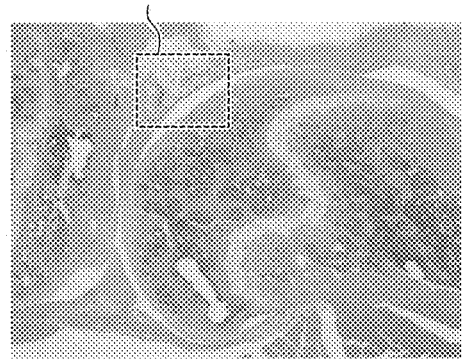
FIGS. 13(A) and 13(B) are photographs of the pathological sample of the tissue of the left knee joint of a mouse model of collagen arthritis of a paramylon group in Test Example 2.
Figure 13B:
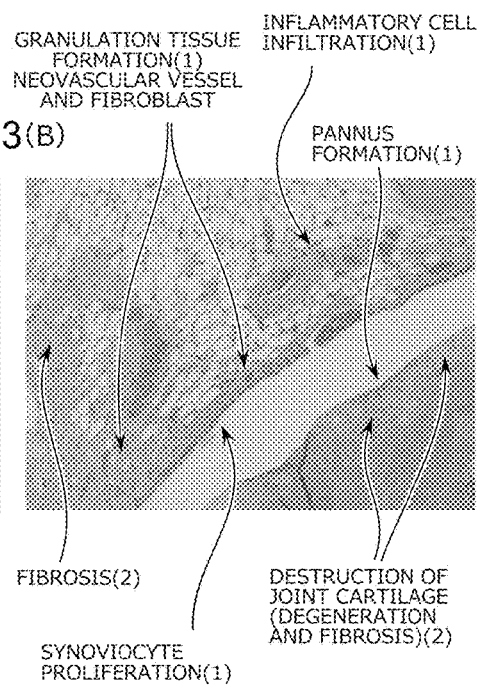

In the paramylon group illustrated in FIGS. 13(A) and 13(B), the synovial membranes had inflammation, granulation tissue formation, and fibrosis rated as very mild (rating 1) to mild (rating 2), and the trochlear grooves of the femurs had pannus formation and the cartilage destruction rated as very mild (rating 1) to mild (rating 2).

Figure 15A:
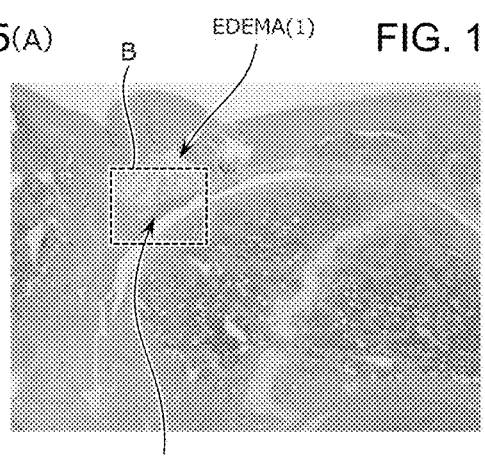
FIGS. 15(A) and 15(B) are photographs of the pathological sample of the tissue of the left knee joint of a mouse model of collagen arthritis of an emulsion paramylon group in Test Example 2.
Figure 15B:
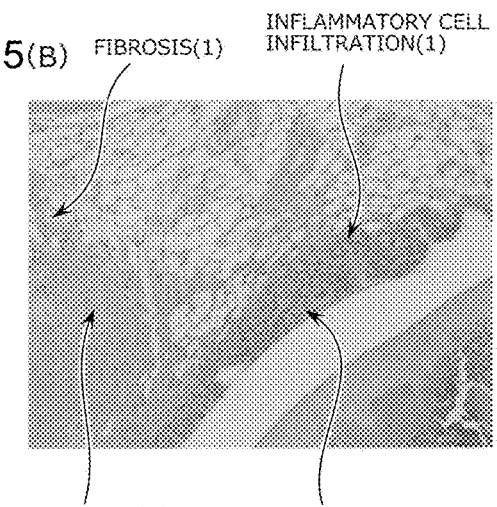

In the emulsion paramylon group illustrated in FIGS. 15(A) and 15(B), the synovial membranes had edema, inflammation, granulation tissue formation, fibrosis, and exudates rated as very mild (rating 1). The trochlear grooves of the femurs had pannus formation and cartilage destruction rated as mild (rating 2).

Measurement of Suppressor T Cells: Th17/Treg

The inguinal lymph nodes removed after 7 weeks from the sensitization day were analyzed on a flow cytometer for distribution of the cell population. The suppressor T cells were measured using Mouse Th17/Treg Phenotyping Kit (BD pharmingen).

FIG. 16 illustrates the number of IL-17 production in CD4 positive T cells, as determined by analysis on the flow cytometer.

FIG. 16 indicates that the paramylon group and the amorphous paramylon group exhibited a smaller number of IL-17A produced, compared with the control group. The emulsion paramylon group exhibited a significantly smaller number, compared with the control group.

Summary of Results in Test Example 1 and Test Example 2

In the control group, the arthritis scores increased over time, and the levels of IgG in the serum increased. In the histopathological study of the knee joints, the synovial membranes had inflammation, granulation tissue formation, fibrosis, and exudates rates as very mild to moderate, and the trochlear grooves of the femurs had pannus formation and cartilage destruction rated as mild.

With regard to the above conditions, the *Euglena* group, the paramylon group, the amorphous paramylon group, and the emulsion paramylon group tended to exhibit low visual scores compared with the control group, and the statistically significant differences were also observed. In the histopathological study, no findings were observed in the *Euglena* group and the amorphous paramylon group except that the synovial membranes had granulation tissue formation rated as very mild. In the paramylon group, although the synovial membranes had inflammation, granulation tissue formation, and fibrosis, and the trochlear grooves of the femurs had pannus formation and cartilage destruction, their extent was less obvious, compared with the control group.

All of the *Euglena* group, the paramylon group, the amorphous paramylon group, and the emulsion paramylon group exhibited decreased secretion of the cytokines in the lymphoid culture supernatant by Anti-CD3, compared with the control group. Particularly, the *Euglena* group and the amorphous paramylon group showed a remarkable reduction.

As described above, the study of the effects of the *Euglena*-derived materials on autoimmune diseases in mouse models of collagen arthritis has revealed that the *Euglena* group, the paramylon group, the amorphous paramylon group, and the emulsion paramylon group had the effect of preventing the onset of arthritis. Particularly, the *Euglena* group and the amorphous paramylon group had a greater prevention effect, which was histologically distinct.

REFERENCE SIGNS LIST a femur
b tibia
c patella
d posterior cruciate ligament
e meniscus
f anterior cruciate ligament

The invention claimed is:

1. A method of treating a human suffering from rheumatoid arthritis comprising administering a therapeutically effective amount of *Euglena* to said human to effectively treat the rheumatoid arthritis in said human.

* * * * *